United States Patent [19]

Jordan

[11] 4,088,682

[45] May 9, 1978

[54] OXALATE HYDROGENATION PROCESS

[76] Inventor: Robert Kenneth Jordan, 3979 Tuxey Ave., Pittsburgh, Pa. 15227

[21] Appl. No.: 592,757

[22] Filed: Jul. 3, 1975

[51] Int. Cl.$^2$ .................. C07C 29/00; C07C 99/00; C07C 51/52

[52] U.S. Cl. .................. 260/534 R; 260/534 E; 260/535 R; 260/535 P; 568/864

[58] Field of Search .......... 260/635 D, 534 R, 534 E, 260/535 R, 535 P

[56] References Cited

U.S. PATENT DOCUMENTS

| | | | |
|---|---|---|---|
| 2,975,218 | 3/1961 | Buchner et al. | 260/635 D |
| 3,478,112 | 11/1969 | Adam et al. | 260/635 D |

OTHER PUBLICATIONS

Carnahan et al., "J. Am. Chem. Soc.", vol. 77 (1955), pp. 3766–3768.

Clark, "J. Phys. Chem.", (8) 1971, pp. 2597–2601.

Primary Examiner—Joseph E. Evans

[57] ABSTRACT

A process for the production of ethylene glycol, alkali metal salts of glycine, alkali metal salts of glycolic acid, alkali metal salts of diglycolic acid and alkali metal salts of nitrilotriacetic acid by the hydrogenation of oxalic acid or an alkali metal hydrogen oxalate, optionally in the presence of ammonia, said oxalic acid or alkali metal hydrogen oxalate containing less than 2 moles water of hydration.

13 Claims, No Drawings

OXALATE HYDROGENATION PROCESS

This invention relates to a process for the hydrogenation oxalic acid and ammonium and metal acid oxalates to salts of hydroxyacetic acid, hydroxyacetic acid, salts of nitrilotriacetic, nitrilotriacetic acid and ethylene glycol.

Ethylene glycol is now made by the hydrolysis of ethylene oxide which in turn is made by the catalyzed oxidation of ethylene using air or oxygen. But there are numerous problems of yields and costs associated with the overall process that have long defied solution. First of all ethylene must be made from natural gas liquids or naphthas in very expensive facilities, made so by high temperature cracking furnaces and sophisticated separation columns. Secondly, in the oxidation of ethylene over known catalysts, i.e., silver, the yields are usually about 85 percent. Further, useless carbon dioxide is made as a by-product. Finally, in the hydrolysis of ethylene oxide to ethylene glycol, diethylene glycol and triethylene glycol are unavoidable and less desirable co-products.

Until recently, some ethylene glycol was made by the hydrogenation of hydroxyacetic acid over various catalysts and in turn the hydroxyacetic acid was made by the addition of carbon monoxide to aqueous formaldehyde (about 37 percent). As formaldehyde is made from expensive methanol and also as carbon monoxide has heretofore been expensive from either of the oxygen partial oxidation of coal or coke, or, from reformed natural gas, it is clear why this route to ethylene glycol has fallen into disuse.

As noted, hydroxyacetic acid was previously made by the addition of carbon monoxide to aqueous formaldehyde. Salts are made by neutralization with a metal or ammonium hydroxide or carbonate. Hydroxyacetic acid is useful in the making of polyesters which in turn have a number of uses, for example surgical threads. Salts of hydroxyacetic acid are useful intermediates in the preparation of esters of hydroxyacetic acid and also as chelating agents.

Nitrilotriacetic acid and certain of its salts, especially sodium salt, are very effective chelating agents, especially useful as replacements for phosphate builders of detergent compositions. Phosphates are known to contribute to the phenomena of "algae blooms" in relatively still waters resulting in oxygenless water. The commercial processes for the production of sodium nitrilotriacetate are based on expensive intermediates including caustic soda, hydrogen cyanide and formaldehyde.

In a number of copending applications I describe and disclose a new technology for the production of oxalates based on salt and cheap carbon monoxide from a blast furnace or modified iron furnace. Application Ser. No. 497,040 filed Aug. 13, 1974, now abandoned, and entitled A PROCESS FOR CARBOXAMIDE CO-PRODUCTS OF FERROUS METALS discloses the conversion of said carbon monoxide to ammonium formate and application Ser. No. 433,296 filed Jan. 14, 1974, now U.S. Pat. 4,034,037 and entitled CARBOXYLATE METALLATION PROCESS discloses the conversion of said ammonium formate and salt directly to anhydrous sodium formate. Anhydrous sodium formate is known to fuse at 400° C to sodium oxalate, hydrogen being a coproduct. Thus with cheap metal oxalates and oxalic acid it is desirable to produce chemicals heretofore based on petroleum. In other copending applications processes for the utilization of metal oxalates and oxalic acid are disclosed, but it is especially important to apply this technology to the production of petrochemicals now based on ethylene to provide said chemicals at a lower cost and with the conservation of energy.

Therefore, it is an object of my invention to provide an improved process for the production of ethylene glycol.

It is another object to provide a new and improved process for the production of sodium nitrilotriacetate.

My invention is a process for the production of at least one of ethylene glycol, alkali metal salt of glycolic acid, alkali metal salt of glycine, alkali metal salt of diglycolic acid and alkali metal salt of nitrilotriacetic acid wherein oxalic acid or alkali metal hydrogen oxalate, containing less than 2 moles water of hydration is catalytically hydrogenated, optionally in the presence of ammonia, at a temperature in the range of from about 50° to about 500° C.

I have unexpectedly discovered that the hydrogenation of oxalic acid or its alkali hydrogen salt in the form of essentially anhydrous compounds gives high yields of reduction products. Thus using anhydrous oxalic acid under hydrogenation conditions like those described by Carnahan, Ford, Grigsby and Hager of JACS 77, 3766–8 (July 20, 1955) one obtains a yield of over 75 percent whereas the yield reported by them was les than 50 percent using oxalic acid dihydrate. The conditions were 145° C at 800 atmospheres using about 1 percent ruthenium dioxide catalyst. As it is known that oxalic acid is decomposed by its reduction product, ethylene glycol as reported by Clark, Journal of Physical Chemistry 71(8),2599–2601, it is clear that water itself is a important factor in this decomposition. Further, that although it is an unavoidable by-product of oxalic acid hydrogenation, its concentration should be minimized in so far as possible. And this is made even more evident by the results of the same experiment using anhydrous oxalic acid and tetrahydrofuran, 50 ml., which results in a yield of at least 85 percent, presumably improved because of the assumed partial solubilization of the oxalic acid.

While large increases in yield have been shown here, it is obvious that in the commercialization of the production of ethylene glycol through the hydrogenation of oxalic acid even small increases are important to the economics. While a large number of catalysts are known and reported for the hydrogenation of carboxylic acids to the corresponding hydroxyl compound, in the hyrogenation of oxalic acid its tendency to decompose at relatively low temperatures requires the selection of catalysts which either results in low temperature hydrogenation or provides a high rate of hydrogenation at higher temperatures. Thus the platinum group metals and their compounds are preferred, but other hydrogenation catalysts may be used.

Another experiment was conducted in which oxalic acid dihydrate was the starting material and the conditions were essentially the same as above, but once every half hour the pressure was reduced to atmospheric pressure to allow any water present to come off. In other words simulating continuous water removal in so far as possible with the equipment available. Here the yield again was 75 percent which again compares to the 47 percent reported by Carnahan etal noted above. The yield of 75 percent under these conditions is especially surprising in that the temperature was maintained throughout at 140°–5° C only a few degrees below the sublimation temperature of oxalic acid, 157° C, though well below the melting point of 189.5° C.

Dreyfus in U.S. Pat. No. 1,962,140 of June 12, 1934 discloses the hydrogenation of oxalic acid to glycolic acid and the alkali metal mono salts of oxalic acid to alkali metal salts of glycolic acid. Using his example, but with a copper-nickel catalyst obtained by the low temperature decomposition (about 300° C) of the coprecipitated anhydrous oxalates, only a few percent of potassium glycolate was obtained using temperatures of 140° to 200° C. It should be noted that Dreyfus did not specify temperature and potassium oxalate concentration, and not even hydrogen pressure. Using 256 g. (2 moles) of anhydrous potassium hydrogen oxalate, 150 g. tetrahydrofuran and 7.5 g of the same catalyst at 170° C gave a yield of 50 percent potassium glycolate at pressures ranging from 100 to 1000 atmospheres hydrogen. Again using a ruthenium dioxide catalyst under about the same conditions much higher conversions were obtained, but the yield obtained using a solution of 17 g. potassium acid oxalate in 100 ml. of water versus that of 17 g potassium acid oxalate (anhydrous) in diethyl ether under the same conditions of 150° C and 800 atmospheres for 6 hours was 25 percent (or less) versus 70 percent or more, however some of the product obtained using an anhydrous system was in the form of the ether, $O(CH_2COOK)_2$ and counted as part of the yield.

Because of the presence of the ether, it was decided to add ammonia to the hydrogen supplied, rather in the same port, once the hydrogenation was under way in the hydrogenation of the potassium acid oxalate (anhydrous) in THF. The product was practically exclusively the potassium salt of nitrilotriacetic acid in over 50 percent yield in spite of the fact that there was a seal problem in the autoclave. Likewise sodium acid oxalate was hydrogenated under the same conditions but on a smaller scale with and without ammonia and the disodium salt of oxybis(acetic acid) and the sodium salt of nitrilotriacetic acid were obtained in over 50 percent yields. This was especially surprising in the case of the oxybis(acetic acid) salt because a yield of almost 50 percent sodium glycolate was obtained at the same time. While the experiment was conducted on a smallish scale, there can be no question but what the total yield, i.e., of glycolic and oxybis(acetic acid) sodium salts was nearly quantative. Clearly, if water removal is conducted during the process oxybis(acetic acid) alkali metal salt would be obtained almost exclusively. Oxybis(acetic acid) is also known as diglycolic acid and its alkali metal salts have been proposed as substitites for alkali metal polyphosphates in detergent compositions.

As no references were found on the production of nitrilotriacetic acid salts and diglycolic acid salts by the above processes, it was decided use varying concentrations of water, without removal, at varying temperatures using potassium acid oxalate and of course, with and without ammmonia depending on the product desired. It was found that at somewhat above 200° C the salt of diglycolic acid begins to form regardless of the amount of water present, although again the yield is not as high as obtained using anhydrous starting material. At 300° C the formation of diglycolic acid salt was clearly a function of residence time, initially glycolic acid salt being formed, but rather rapidly converting to diglycolic acid. This is surprising in view of Dreyfus, U.S. Pat. No. 1,999,403 in which example an aqueous solution of potassium ethyl oxalate is hydrogenated at about 300° C at 100–150 atmospheres hydrogen pressure over a nickel catalyst. It would appear that the temperature of 300° C at which the nickel catalyst was formed was also the temperature of hydrogenation since no other is mentioned in the example (a much lower temperature noted in example 2). What is certain is that at about 300° C the residence time should be less than 2 hours to achieve a high proportion of potassium glycolate versus the potassium salt of diglycolate.

When an excess of water is present in the hydrogenation of an alkali metal hydrogen oxalate in the presence of ammonia there is a choice of adding the ammonia before or during the hydrogenation. When it is added before, the rate of hydrogenation appears to be slower than on addition as the process is conducted. This is even more evident when essentially anhydrous starting materials are used. Using an excess of water at lower temperatures, about 125° C, reasonable yields of the alkali metal salt of glycine can be obtained, though even at these conditions the corresponding condensation product, the alkali metal salt of nitrilotriacetic acid is present in a significant concentration. As the amount of water is reduced the concentration of glycinate decreases at the expense of the nitrilotriacetate, but at 125° C some glycinate is present even when substantially all the water is removed. At somewhat above 200° C only a small concentration of the glycinate is obtained, the dominant product being the nitrilotriacetate even in the presence of water. Glycine is a useful protein.

The process of hydrogenating oxalic acid or alkali metal hydrogen oxalates is seemingly facilitated by the use of inert solvents, probably because a degree of dissolution is achieved. Thus cyclohexane, diethyl ether and tetrahydrofuran gave increased rates, especially when the water concentration was low. It is especially ideal to utilize a liquid in the practice of conducting the hydrogenation on a continuous process, although it is well known that oxalic acid in the anhydrous form has a melting point of 190° C and even very small concentrations of water significantly lowers its melting temperature. Thus it is not necessary to utilize a solvent for continuous operation, yet there is the fact that at about 140–45° C the rate was improved using anhydrous oxalic acid in THF and also in diethyl ether. It is also reported in the handbooks that oxalic acid decomposes on melting at 190° C, but hydrogenation was achieved well above that temperature.

As mentioned earlier, it is known that oxalic acid is decomposed in the presence of ethylene glycol, its hydrogenation product. To over come this particular problem an experiment was conducted in which oxalic acid was hydrogenated to ethylene glycol in two distinct steps. First sodium hydrogen oxalate was hydrogenated at 140°–145° C to sodium glycolate and then oxalic acid was added. Being a stronger acid, the oxalic acid was converted to sodium hydrogen oxalate and the sodium glycolate was converted to glycolic acid. This mixture was hydrogenated so that the resulting mixture was sodium glycolate in ethylene glycol which is easily separated so that the process can be continued using the sodium glycolate with more oxalic acid. Obviously this process too is ideally conducted on a continuous basis and water may or may not be removed as the process progresses. The yield of ethylene glycol obtained in the experiment in which water was removed after the first step before the addition of oxalic acid, was about 80 percent.

Ideally noble metal hydrogenation catalysts are employed, ideally ruthenium or ruthenium dioxide or other of its compounds. Other platinum group metals, oxides and compounds generate well, but appear to be less effective. Transition metals and their compounds are also operable, especially nickel, but appear to be also less effective than ruthenium dioxide.

According to the provision of the patent statutes, I have explained the principle of my invention and have described and illustrated what I now consider to represent its best embodiment. However, I desire to have it understood that within the scope of the appended claims, the invention may be practiced otherwise than as specifically illustrated and described.

I claim:

1. A process for the production of ethylene glycol comprising hydrogenating oxalic acid containing less than 2 moles water per mole of oxalic acid at a temperature in the range of from about 50° to about 500° C.

2. The process of claim 1 comprising water removal during the process.

3. A process for the production of alkali metal glycolates comprising hydrogenating an alkali metal hydrogen oxalate containing less than two moles water per mole of oxalate at a temperature in the range of from about 50° to about 500° C.

4. The process of claim 3 where the alkali metal hydrogen oxalate is sodium hydrogen oxalate.

5. The process of claim 3 comprising water removal during to process.

6. A process for the production of alkali metal salts of oxybis(acetic acid) comprising hydrogenating an alkali metal hydrogen oxalate at a temperature in the range of from about 50° to about 500° C.

7. The process of claim 6 comprising water removal during the process.

8. A process for the production of alkali metal salts of glycine comprising hydrogenating an alkali metal hydrogen oxalate in the presence of ammonia at a temperature in the range of from about 50° to about 300° C.

9. A process for the production of alkali metal salts of nitrilotriacetic acid comprising hydrogenating an alkali metal ammonium oxalate or an alkali metal hydrogen oxalate in the presence of ammonia at a temperature in the range of from about 50° to about 400° C.

10. The process of claim 9 comprising water removal during the process.

11. A process for the production of ethylene glycol comprising,
    a. hydrogenating an alkali metal hydrogen oxalate to an alkali metal glycolate,
    b. adding oxalic acid to provide alkali metal hydrogen oxalate and glycolic acid,
    c. hydrogenating to obtain a mixture of alkali metal glycolate and ethylene glycol and recovering said ethylene glycol therefrom.

12. The process of claim 11 comprising water removal during the process.

13. The process of claim 11 conducted continuously.

* * * * *